United States Patent [19]

Masquelier et al.

[11] Patent Number: 4,868,158

[45] Date of Patent: Sep. 19, 1989

[54] METHOD FOR THE PRODUCTION OF A MACROMOLECULAR CARRIER LOADED WITH A BIOLOGICALLY ACTIVE SUBSTANCE

[75] Inventors: Michele Masquelier, Huddinge; Mikael Ros, Stockholm; Curt Peterson, Hägersten; Mats Rudling; Sigurd Vitols, both of Stockholm, all of Sweden

[73] Assignee: Oncholab AB, Stockholm, Sweden

[21] Appl. No.: 30,861

[22] PCT Filed: Jun. 17, 1986

[86] PCT No.: PCT/SE86/00291

§ 371 Date: Feb. 12, 1987

§ 102(e) Date: Feb. 12, 1987

[87] PCT Pub. No.: WO86/07539

PCT Pub. Date: Dec. 31, 1986

[30] Foreign Application Priority Data

Jun. 17, 1985 [SE] Sweden ............................... 8502998

[51] Int. Cl.$^4$ ...................... A61K 37/02; C07K 15/16
[52] U.S. Cl. .................................. 514/21; 424/85.8; 424/86; 424/87; 436/518; 436/535; 436/543; 530/359; 530/387; 514/773
[58] Field of Search .................. 530/387, 359; 424/85, 424/86, 87, 858; 514/773, 21

[56] References Cited

U.S. PATENT DOCUMENTS

| | | | |
|---|---|---|---|
| 4,096,136 | 6/1978 | Ayers et al. | 530/359 |
| 4,186,192 | 1/1980 | Lundblad et al. | 424/101 X |
| 4,356,117 | 10/1982 | Neville et al. | 530/359 X |
| 4,440,679 | 4/1984 | Fernandes et al. | 530/387 X |
| 4,478,829 | 10/1984 | Landaburu et al. | 424/101 X |
| 4,565,651 | 1/1986 | Ohmura et al. | 514/8 X |
| 4,603,010 | 7/1986 | Ayers et al. | 530/359 |

OTHER PUBLICATIONS

Masquelier et al., Cancer Research, 46:3842–3847 (1986).
Krieger et al., J. Biol. Chem., 253, 4093–4101 (1978).
Krieger et al., J. Biol. Chem., 254, 3843–3853 (1979).
B. Blomback et al., Plasmaproteiner, Stockholm, 1976, p. 89.
Firestone et al., "Selective Delivery of Cytotoxic Cpds", J. Med. Chem., vol. 27 (1984), pp. 1037–1043.
M. C. Berenbaum, "Time–Dependence and Selectivity . . . ", Immunology, vol. 36 (1979), pp. 355–356.
J. E. Lovelock, "The Denaturation of Lipid–Protein Complexes . . .", Proceedings of the Royal Soc (London), Ser B, 147 (1957), pp. 427–433.
A. Gustafson, "New Method for Partial Delipidization . . .", J. of Lipid Research, vol. 6, No. 4 (1965), pp. 512–517.
M. J. Rudling et al., "Delivery of Aclacinomycin . . .", Cancer Research, vol. 43, No. 10 (1983), pp. 4600–4605.

Primary Examiner—Howard E. Schain
Attorney, Agent, or Firm—Bert J. Lewen; Henry Sternberg

[57] ABSTRACT

The invention relates to a method for the preparation of a carrier loaded with lipophilic biologically active substance based on reconstituted LDL (Low Density Lipoprotein), wherein (1) LDL is lyophilized in the presence of a protective agent; (2) the lyophilized LDL is extracted with an organic solvent; (3) the biologically active substance solubilized in a solvent is incubated with extracted LDL; the solvent is evaporated and the reconstituted LDL solubilized in an aqueous buffer; the non-incorporated biologically active substance is separated from the LDL-complex, characterized in that in step (1) the protective agent is a monosaccharide, a disaccharide, a water-soluble polysaccharide, a sugar alcohol or a mixture of these and in step (3) optionally the extract obtained during the extraction of the lyophilized LDL is mixed with the lipophilic biologically active substance solubilized in an organic solvent and this mixture is then incubated with the LDL. Preferred protective agents are sucrose, glucose and fructose. The reconstituted LDL obtained by the claimed process have properties similar to native LDL in vitro and in vivo.

14 Claims, 2 Drawing Sheets

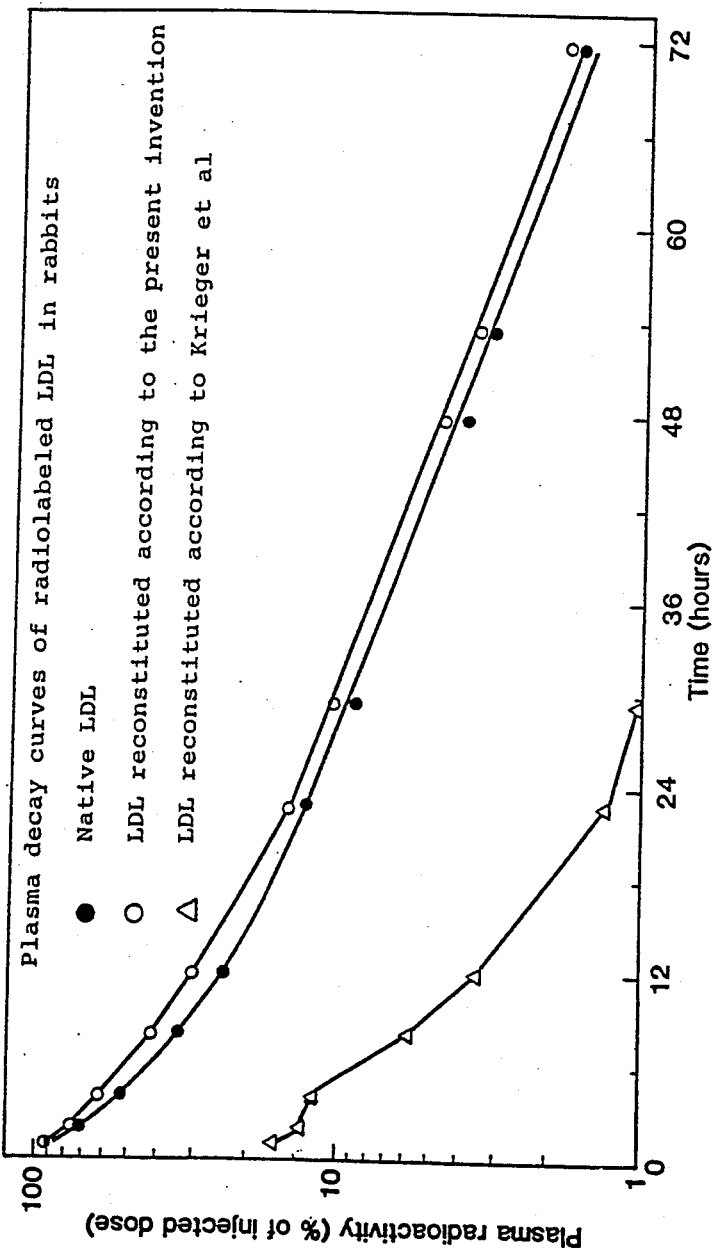

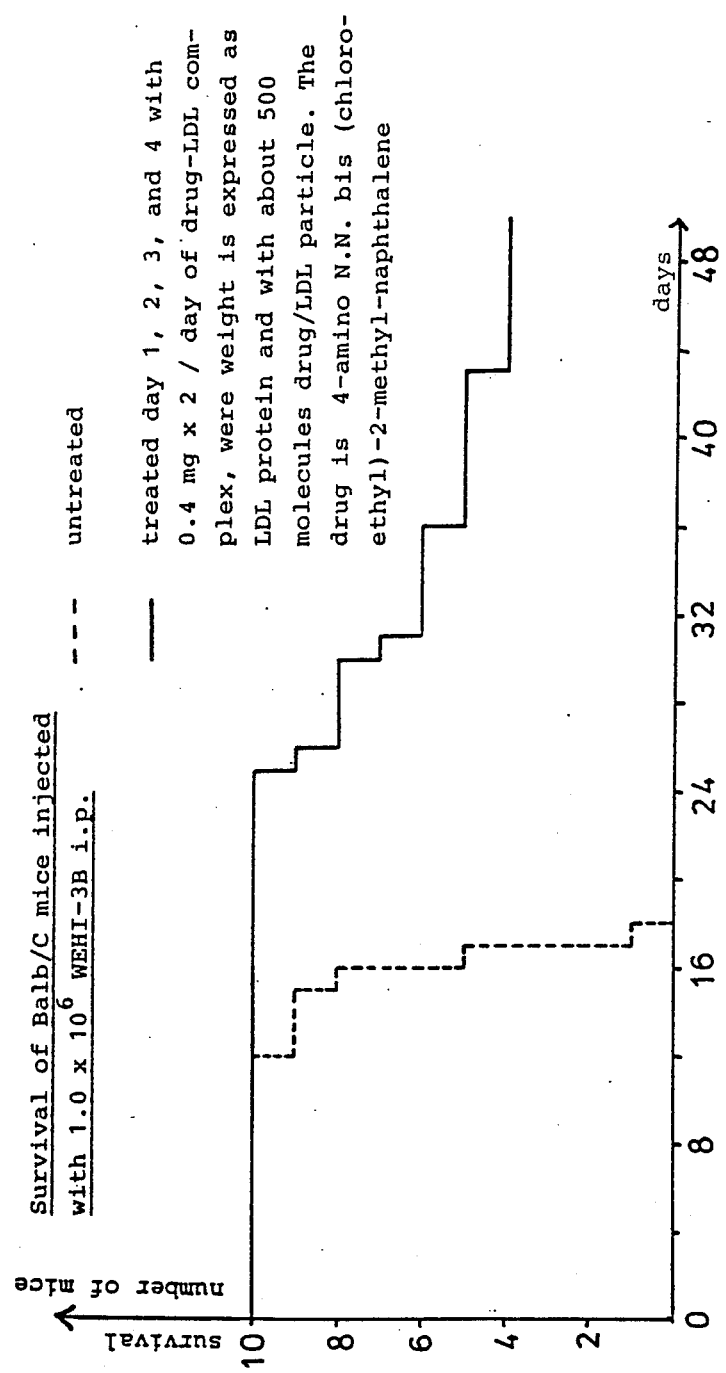

METHOD FOR THE PRODUCTION OF A MACROMOLECULAR CARRIER LOADED WITH A BIOLOGICALLY ACTIVE SUBSTANCE

The present invention relates to a method for the preparation of a carrier for a biologically active substance, below called drug, based on the reconstitution of LDL (Low Density Lipoprotein).

The term "biologically active substance", or "drug", is used in its most wide definition and includes substances such as pharmaceutically active substances, enzymes, toxins, radiosensitizers, radioactive substances etc.

Many attempts have been made to increase the concentration of a biologically active substance, for example an antitumoral drug, in a certain organ or in certain target cells in order to increase the efficacy of the treatment and reduce the side effects.

One way to accomplish this is to link the drug to a carrier, for example, a macromolecule. The rationale is that the macromolecule should have a high uptake by the target cell or that the linkage carrier/drug in other aspects would give a better efficacy than would be the case with the free drug.

A number of macromolecules have been investigated with respect to their use as carriers, such as DNA, liposomes, red blood ghost cells, lectines, different proteins such as antibodies, peptide hormones, and glucoproteins. Other molecules such as estrogens have as well been tried.

If a biologically active substance could be linked or incorporated to the LDL particle in such a way that the reconstituted LDL behaves like native LDL with respect to LDL-receptor mediated uptake and biological half-life in plasma, the substance could be targetted to cells expressing high levels of LDL-receptors. Due to the long half-life of LDL the system could as well act as a slow release system for appropriate substances.

Krieger et al (J. Biol. Chem. 253 (1978) 4093–4101 and J. Biol. Chem. 254 (1979) 3843-3853) have described a reconstitution procedure. Their method in brief is that LDL is lyophilized in the presence of unsoluble potato starch, and the neutral lipids are extracted with an organic solvent such as heptane. The substance to be incorporated is solubilized in an organic solvent and incubated with the lipid-depleted LDL. After evaporation of the organic solvent the reconstituted LDL is solubilized in an aqueous buffer.

Even if the reconstituted LDL particle according to the method of Krieger et al shows LDL receptor mediated uptake in vitro, it can not be used in vivo since the reconstituted particles are rapidly taken up by the cells of the reticuloendothelial system in liver and spleen.

We have unexpectedly found a modified reconstitution procedure that gives a reconstituted LDL-particle with almost the same properties as native LDL both in vitro and in vivo.

The present invention relates to a procedure for the preparation of a carrier loaded with a biologically active substance on the basis of reconstituted LDL, where (1) LDL is lyophilized in the presence of a protecting agent; (2) the lyophilized LDL is extracted with an organic solvent; (3) the biologically active substance is solubilized in a solvent and incubated with the extracted LDL; (4) the solvent is evaporated; (5) the reconstituted LDL is solubilized in an aqueous buffer, and (6) the non-incorporated substance is separated from the LDL-complex. In the procedure in step (1) the protective agent is a monosaccharide, a disaccharide, a water-soluble polysaccharide, a sugar alcohol or a mixture of these and in step (3) optionally the extract obtained during the extraction of the lyophilized LDL is mixed with the lipophilic biologically active substance solubilized in an organic solvent and this mixture is then incubated with the LDL.

The method according to the present invention is different from the method of Krieger et al mainly in the use of the protective substance. In step (1) Krieger is using potato starch as a protective agent. Potato starch is a water-insoluble polysaccharide with high molecular weight. In our method we are using as a protective agent a monosaccharide, a disaccharide, a water-soluble polysaccharide, a sugar alcohol or a mixture of these.

In order to investigate plasma clearance, human LDL was injected intravenously in mice (Balb/C) and the percentage of injected dose remaining in plasma was determined after 90 minutes. The percentage of native LDL remaining in plasma after 90 minutes is about 59. The percentage of LDL reconstituted according to the method of Krieger et al remaining in plasma was very low, less than 3. The percentage remaining in plasma according to the present invention have values of 57–58, which is a very surprising and technically important development.

The plasma clearance in rabbits was determined from plasma decay curves for radiolabeled LDL: for native LDL, reconstituted LDL according to the method of Krieger et al and reconstituted LDL according to the method of the present invention. As can be seen from FIG. 1, native LDL and the reconstituted LDL according to the present invention had the same clearance, while the reconstituted LDL according to Krieger et al disappeared rapidly from plasma.

The particle sizes of various preparations of LDL resolubilized in buffer have been determined by means of quasielectric light scattering. It was found that the apparent mean hydrodynamic radius of lyophilized LDL without any protective substance was about 2.9 times larger than that for native LDL, and LDL lyophilized in the presence of potato starch as protective substance had a radius of about 2.7 times, while LDL lyophilized in the presence of sucrose had a radius about 1.2 times that of native LDL. The drug-LDL complex according to the method of Krieger had an apparent mean hydrodynamic radius of about 3.8 times the value for native LDL, while the reconstituted drug-LDL complex according to the present invention had a radius of about 1.3 times that of native LDL.

The reconstitution method of Krieger et al is based on a method developed by A. Gustafson (J. Lipid Res. 1965, 6, 512-517) to extract the cholesteryl esters from the core of LDL. The key step in this procedure is to use potato starch to stabilize the lipid-depleted apoproteins during the lyophilization and heptane extraction of the neutral lipids from the core of the LDL.

As shown above the method of Krieger et al will not give sufficient protection of the LDL. Important for the reconstitution of the LDL particle is the replacement of an appropriate amount of the neutral lipids in the core with the desired substance, or drug. If the drug-LDL complex should be used for targetting via the LDL receptor pathway and too much of the drug is inserted into the LDL particle there is a risk for the drug leaking out when the LDL particle is colliding with different cells in the blood and the blood vessels. This gives an unspecific uptake of the drug and in this case the incorporated drug-LDL complex functions as a slow release system. A suitable protective substance should prevent aggregation of the LDL particles or other damages such as the falling apart of the particle and prevent too high a replacement of the lipids from the LDL particle.

If the amount of protective substance used is too small, then the resulting reconstituted LDL particle will have a rapid clearance from plasma; this effect is not linear, and the amount of protective substance should be at least 1 mg/mg LDL, where LDL is measured as protein. the other hand, if the amount of protective substance is too high then the amount of drug incorporated will be too low; this means that there exists a certain range for the amount of protective substance used.

Protective substances fulfilling the above criteria are water-soluble saccharides such as monosaccharides, disaccharides, trisaccharides, water soluble polysaccharides, sugar alcohols or mixtures of these.

Examples of monosaccharides, that can be used according to the present invention are: glucose, mannose, glyceraldehyde, xylose, lyxose, talose, sorbose, ribulose, xylulose, galactose and fructose. Examples of disaccharides are sucrose, trehalose, lactose and maltose. Examples of trisaccharides are raffinose. Among water-soluble polysaccharides certain water-soluble starches and celluloses can be mentioned. Examples of sugar alcohols are glycerol.

Preferred protective agents in the present invention are sucrose, glucose or fructose which give a LDL complex behaving like native LDL.

The organic solvent used in step (2) for the extraction of the lyophilized LDL is preferably a non-polar solvent such as heptane or carbon tetrachloride. Heptane is the preferred solvent.

The biologically active substance that is incorporated into the lyophilized LDL shall be a lipophilic substance. Examples of such biologically active substances that can be incorporated into the LDL particle according to the present invention are anti-tumoral drugs, drugs affection the cholesterol synthesis, as well as radiosensitizers, enzymes, ensyme inhibitors, radioactive substances, toxins, etc.

The separation of the non-incorporated biologically active substance from the LDL complex and the biologically active substance is done after solubilization in aqueous buffer by known procedures, such as centrifugation, filtration etc.

The invention is illustrated in the following examples, where the temperature is given in centigrade.

The LDL used in the examples was human LDL (density 1.019–1.063), obtained by ultracentrifugation of plasma from healthy human volunteers. All LDL amounts refer to protein according to the method of Lowry et al, J. Biol. Chem. 193 (1951) 265–275 where bovine serum albumin is used as standard. The biologically active substance used is the anti-tumoral drug AD-32, N-trifluoroacetyladriamycin-14-valerate. The in vivo tests were performed on Balb/C mice. cl EXAMPLE 1

2 mg LDL (400 microliter of liquid) were, after dialysis with 0,3 mM Na EDTA, transferred to a siliconized glass tube and 100 mg sucrose was added. The solution was rapidly frozen at −50 C in ethanol and lyophilized for 5–6 hours. The dried preparation was extracted three times with 5 ml of heptane. The heptane phases were pooled and evaporated. 2 mg of AD-32 in 0.5 ml of anhydrous diethyl ether were then added to the dried extracts. The solution was mixed with the extracted LDL by gentle agitation, and incubated at 4 C for 15 minutes. The solvent was evaporated under nitrogen, the drug-LDL complex was solubilized by the addition of 1 ml 10 mM Tricine, pH 8,4. Insoluble, non-incorporated drug was separated by centrifugation for 5 minutes in a Beckman microfuge. This gave a reconstituted LDL particle containing 110–130 molecules of AD-32 per LDL particle. The percentage remaining in plasma in Balb/C mice was about 58 after 90 minutes.

EXAMPLE 2

Like example 1, but the lyophilized LDL was not extracted by heptane, instead AD-32 solubilized in ether was added directly. This gave about 35–43 molecules AD-32 per LDL particle and percentage remaining in plasma of about 55.

EXAMPLE 3

Like example 1, but instead of sucrose as a protective agent 80 microliters of glycerol was used. This gave about 50 molecules AD-32 per LDL and the percentage remaining in plasma was about 55.

EXAMPLE 4

Comparative test I

Like example 1, but instead of sucrose 25 mg potato starch was used. The extract obtained after the extraction of LDL was discarded and AD-32 in anhydrous ether was added directly to the extracted LDL. (Method of Krieger et al). This gave about 400 molecules of AD-32 per LDL, but the percentage of injected dose remaining in plasma was below 3.

EXAMPLE 5

Comparative test II

Like example 1 but 25 mg of potato starch and 80 microliters of glycerol was used instead of sucrose. This gave about 50 molecules AD-32 per LDL particle and the percentage remaining in plasma was about 50.

Therapeutic test 1

In this test the drug AD-32 was used. The amount AD-32 administered in this test was well below the toxic level for the mice and the result is presented here to give an example of the targetting effect of the drug-LDL complex compared to free drug. Balb/C mice were injected intraperitonally (i.p.) with 1.0 million WEHI-3B cells, a murine monomyelocytic cell line. No difference (2%) was found in survival (ILS, Increased Life Span) between the controls and the group treated with 1.9 mgAD-32/kg/day for five days. The AD-32 was administered i.p. dissolved in a mixture of ethanol and castor oil. The mice that obtained the same dose of AD-32 incorporated into LDL according to the procedure in Example 1 administered i.p. for five days had a 26% increase in life span.

Therapeutic test 2

Balb/C mice were injected i.p. with 1.0 million WEHI-3B cells and an alkylating agent, 4-amino N.N.-bis (chloroethyl)-2-methyl-naphthalene, was incorporated according to the present method. The animals were treated for four consecutive days i.p. and the result is shown in FIG. 2. The control group died during days 12–18, while in the treated group they died from day 25, with 50% still living on day 42 and 40% still surviving (on day 50).

We claim:

1. A method for the preparation of a carrier loaded with a lipophilic biologically active substance which comprises:
   (1) lyophilizing LDL in the presence of a protective agent selected from monosaccharides, disaccharides, water-soluble polysaccharides, a sugar alcohol or a mixture thereof;
   (2) incubating the lyophilized LDL with a lipophilic biologically active substance solubilized in a non-polar solvent to reconstitute the LDL and form an LDL-complex with at least part of the biologically active substance, said complex having a plasma clearance substantially the same as native LDL;
   (3) evaporating the non-polar solvent from the reconstituted LDL and solubilizing the reconstituted LDL in an aqueous buffer; and
   (4) separating the lipophilic biologically active material, if any, which did not form part of the LDL complex.

2. The method of claim 1 wherein the lyophilized LDL from step (1) is extracted with an organic solvent and the extracted LDL is incubated in accordance with step (2).

3. The method of claim 1 wherein the lyophilized LDL from step (1) is extracted with an organic solvent to form an extract; the organic solvent is separated from the extract to form dried LDL; and the dried LDL is incubated in accordance with step (2).

4. The method of claim 1, 2 or 3 wherein the protective agent is glyceraldehyde, xylose, lyxose, raffinose, glucose, mannose, galactose, talose, ribulose, xylulose, trehalose, fructose, sorbose, maltose, lactose, sucrose, glycerol or a mixture thereof.

5. The method of claim 4 wherein the protective agent is sucrose.

6. The method of claim 4 wherein the protective agent is glucose.

7. The method of claim 4 wherein the protective agent is fructose.

8. The method of claim 2 or 3 wherein the organic solvent is n-heptane.

9. The method of claim 1, 2 or 3 wherein the solvent used in step (2) for the solubilization of the lipophilic biologically active substance is ethyl ether, heptane, carbon tetrachloride or benzene.

10. The method of claim 1, 2 or 3 wherein the amount of protective agent is in the range of 0.5 to 100 mg/mg LDL, where LDL is measured as protein.

11. A complex of a lipophilic biologically active substance and a carrier, said complex being substantially free of non-complexed biologically active substance and being solubilized in an aqueous buffer, wherein said carrier is prepared by:
    (1) lyophilizing LDL in the presence of a protective agent selected from monosaccharides, disaccharides, water-soluble polysaccharides, a sugar alcohol or a mixture thereof;
    (2) incubating the lyophilized LDL with a lipophilic biologically active substance solubilized in a non-polar solvent to reconstitute the LDL and form an LDL-complex with at least part of the biologically active substance, said complex having a plasma clearance substantially the same as native LDL;
    (3) evaporating the non-polar solvent from the reconstituted LDL and solubilizing the reconstituted LDL in an aqueous buffer; and
    (4) separating the lipophilic biologically active material, if any, which did not form part of the LDL complex.

12. The complex of claim 11 wherein the biologically active material is AD-32 and there are from 35 to 130 molecules of AD-32 per LDL particle.

13. A method of treating tumors in humans and animals for diagnostic and therapeutic purposes which comprises administering to said humans or animals a diagnostically or therapeutically effective amount of a complex of a lipophilic biologically active substance and a carrier, said complex being substantially free of non-complexed biologically active substance and being solubilized in an aqueous buffer, wherein said carrier is prepared by:
    (1) lyophilizing LDL in the presence of a protective agent selected from monosaccharides, disaccharides, water-soluble polysaccharides, a sugar alcohol or a mixture thereof;
    (2) incubating the lyophilized LDL with a lipophilic biologically active substance solubilized in a non-polar solvent to reconstitute the LDL and form an LDL-complex with at part of the biologically active substance, said complex having a plasma clearance substantially the same as native LDL;
    (3) evaporating the non-polar solvent from the reconstituted LDL and solubilizing the reconstituted LDL in an aqueous buffer; and
    (4) separating the lipophilic biologically active material, if any, which did not form part of the LDL complex.

14. A method according to claim 11 wherein the biologically active substance is 4-amino-N,N-bis(-chloroethyl)-2-methylnaphthalene.

* * * * *

UNITED STATES PATENT AND TRADEMARK OFFICE
CERTIFICATE OF CORRECTION

PATENT NO. : 4,868,158

DATED : September 19, 1989

INVENTOR(S) : Masquelier et al.

It is certified that error appears in the above-identified patent and that said Letters Patent is hereby corrected as shown below:

Col. 1 above line 32:   Insert

--An ideal carrier link to a drug should fulfil the following criteria:

1. It should permeate through the anatomical barriers separating the administrating site and the target cell, 2. The linkage between the carrier and the drug should be sufficiently stable in the blood, 3. It should not be rapidly cleared from the blood circulation by the reticuloendothelial system in the liver and the spleen, 4. It should be unable to cross the cell membranes by diffusion in order to prevent unspecific uptake by non-target cells, 5. It should interact as selectively as possible with receptors on the target cell surface, 6. Substances which are inactively linked to the carrier but biologically active in the cell should be carried into the cell by the carrier where the linkage should be cleaved, 7. It should be non-immunogenic.

Several proposed carriers, such as liposomes, do not fulfil the third criterion above, i.e. there are cleared rapidly from the blood by the liver and the spleen and hence do not stay for a sufficient time to get the required effect.

LDL, Low Density Lipoprotein, is a macromolecule that has several attractive properties. This lipoprotein is a

UNITED STATES PATENT AND TRADEMARK OFFICE
CERTIFICATE OF CORRECTION

PATENT NO. : 4,868,158
DATED : September 19, 1989
INVENTOR(S) : Masquelier et al.

It is certified that error appears in the above-identified patent and that said Letters Patent is hereby corrected as shown below:

spherical particle with a diameter of approximately 220Å, a density between 1.019 and 1.063 and a molecular weight of approximately 3 megadaltons, and stays in the circulation for 2-3 days in humans. Each LDL particle contains a non-polar core composed of about 1500 cholesterol molecules esterified to long-chain fatty acids. The core is surrounded by a polar coat of cholesterol, phospholipid and apoprotein B, apo B. LDL is the major cholesterol transporter in human plasma, containing about 70% of plasma cholesterol. Mammalian cells have specific LDL receptors on the surface that recognizes the apo B and binds the LDL particle. The LDL particle is then endocytosed and transported to the lysosomes where it is degraded.--

Col. 3, line 12:   after "protein." insert --On--.

Col. 3, line 60:   delete "cl"

Col. 3, lines 61 between 62, insert --Example 1 --

Col. 6, line 50:   change "11" to --1--.

Signed and Sealed this

First Day of January, 1991

Attest:

HARRY F. MANBECK, JR.

Attesting Officer

Commissioner of Patents and Trademarks